United States Patent
Parsche et al.

(10) Patent No.: US 9,376,907 B2
(45) Date of Patent: Jun. 28, 2016

(54) METHOD OF HYDROCARBON RESOURCE RECOVERY INCLUDING ACTUATOR OPERATED POSITIONING OF AN RF SENSOR AND RELATED APPARATUS

(71) Applicant: HARRIS CORPORATION, Melbourne, FL (US)

(72) Inventors: Francis E. Parsche, Palm Bay, FL (US); Mark Trautman, Melbourne, FL (US)

(73) Assignee: HARRIS CORPORATION, Melbourne, FL (US)

( * ) Notice: Subject to any disclaimer, the term of this patent is extended or adjusted under 35 U.S.C. 154(b) by 0 days.

(21) Appl. No.: 14/596,640

(22) Filed: Jan. 14, 2015

(65) Prior Publication Data

US 2015/0122477 A1    May 7, 2015

Related U.S. Application Data

(62) Division of application No. 13/215,760, filed on Aug. 23, 2011, now Pat. No. 8,967,248.

(51) Int. Cl.
| | |
|---|---|
| *E21B 43/24* | (2006.01) |
| *E21B 47/00* | (2012.01) |
| *G01N 27/02* | (2006.01) |
| *E21B 17/02* | (2006.01) |
| *E21B 47/01* | (2012.01) |

(Continued)

(52) U.S. Cl.
CPC ............... *E21B 47/00* (2013.01); *E21B 17/028* (2013.01); *E21B 43/2408* (2013.01); *E21B 47/01* (2013.01); *E21B 47/122* (2013.01); *G01N 27/02* (2013.01); *G01N 33/241* (2013.01); *E21B 43/2406* (2013.01); *G01N 33/24* (2013.01)

(58) Field of Classification Search
CPC .................. E21B 43/2406; E21B 43/2408
USPC .......... 166/248, 272.1, 272.3, 272.7, 302, 60, 166/369, 65.1; 392/301, 306
See application file for complete search history.

(56) References Cited

U.S. PATENT DOCUMENTS

| | | |
|---|---|---|
| 3,164,988 A | 1/1965 | Cook |
| 4,166,504 A | 9/1979 | Brown et al. |

(Continued)

FOREIGN PATENT DOCUMENTS

| | | |
|---|---|---|
| WO | 2009137565 | 11/2009 |

*Primary Examiner* — Jennifer H Gay
*Assistant Examiner* — George Gray
(74) *Attorney, Agent, or Firm* — Allen, Dyer, Doppelt, Milbrath & Gilchrist, P.A.

(57) ABSTRACT

A method of hydrocarbon resource recovery from a subterranean formation may include forming a plurality of spaced apart injector/producer well pairs in the subterranean formation. Each injector/producer well pair may include a laterally extending producer well and a laterally extending injector well spaced thereabove. The method may include forming an intermediate well adjacent a given injector/producer well pair, and operating a positioning actuator to position a radio frequency (RF) sensor coupled to the positioning actuator to at least one predetermined location within the intermediate well. The method may further include operating the RF sensor at the at least one predetermined location within the intermediate well to selectively sense at least one corresponding portion of the subterranean formation adjacent the given injector/producer well pair. The method may also include recovering hydrocarbon resources from the plurality of injector/producer well pairs including the given injector/producer well pair.

14 Claims, 11 Drawing Sheets

(51) Int. Cl.
*E21B 47/12* (2012.01)
*G01N 33/24* (2006.01)

(56) References Cited

U.S. PATENT DOCUMENTS

| | | | |
|---|---|---|---|
| 5,214,384 A | 5/1993 | Sprunt et al. | |
| 5,831,433 A * | 11/1998 | Sezginer et al. | 324/303 |
| 5,874,214 A | 2/1999 | Nova et al. | |
| 5,961,923 A | 10/1999 | Nova et al. | |
| 6,017,496 A | 1/2000 | Nova et al. | |
| 6,025,129 A | 2/2000 | Nova et al. | |
| 6,100,026 A | 8/2000 | Nova et al. | |
| 6,189,611 B1 * | 2/2001 | Kasevich | 166/248 |
| 6,284,459 B1 | 9/2001 | Nova et al. | |
| 6,319,668 B1 | 11/2001 | Nova et al. | |
| 6,372,428 B1 | 4/2002 | Nova et al. | |
| 7,152,685 B2 | 12/2006 | Adnan et al. | |
| 7,193,414 B2 | 3/2007 | Kruspe et al. | |
| 7,426,968 B2 | 9/2008 | Hall | |
| 7,441,597 B2 | 10/2008 | Kasevich | |
| 7,461,691 B2 | 12/2008 | Vinegar et al. | |
| 7,461,693 B2 | 12/2008 | Considine et al. | |
| 7,562,708 B2 | 7/2009 | Congliandro et al. | |
| 7,640,133 B2 | 12/2009 | Monmont et al. | |
| 7,677,673 B2 | 3/2010 | Tranquilla et al. | |
| 7,703,317 B2 | 4/2010 | Goodwin et al. | |
| 7,798,220 B2 | 9/2010 | Vinegar et al. | |
| 7,845,219 B2 | 12/2010 | Goodwin et al. | |
| 7,975,763 B2 * | 7/2011 | Banerjee et al. | 166/248 |
| 2007/0261844 A1 | 11/2007 | Cogliandro et al. | |
| 2009/0050318 A1 | 2/2009 | Kasevich | |
| 2009/0139716 A1 | 6/2009 | Brock et al. | |
| 2009/0200016 A1 * | 8/2009 | Goodwin et al. | 166/248 |
| 2010/0078163 A1 | 4/2010 | Banerjee et al. | |
| 2010/0294488 A1 | 11/2010 | Wheeler et al. | |
| 2010/0294489 A1 | 11/2010 | Dreher, Jr. et al. | |
| 2011/0120710 A1 | 5/2011 | Dong et al. | |
| 2012/0061080 A1 | 3/2012 | Sultenfuss et al. | |
| 2012/0125608 A1 | 5/2012 | Parsche | |
| 2013/0048277 A1 | 2/2013 | Parsche et al. | |
| 2013/0048278 A1 | 2/2013 | Parsche et al. | |
| 2013/0192825 A1 | 8/2013 | Parsche | |

* cited by examiner

METHOD OF HYDROCARBON RESOURCE RECOVERY INCLUDING ACTUATOR OPERATED POSITIONING OF AN RF SENSOR AND RELATED APPARATUS

FIELD OF THE INVENTION

The present invention relates to the field of hydrocarbon resource recovery, and, more particularly, to hydrocarbon resource recovery using RF heating.

BACKGROUND OF THE INVENTION

Energy consumption worldwide is generally increasing, and conventional hydrocarbon resources are being consumed. In an attempt to meet demand, the exploitation of unconventional resources may be desired. For example, highly viscous hydrocarbon resources, such as heavy oils, may be trapped in tar sands where their viscous nature does not permit conventional oil well production. Estimates are that trillions of barrels of oil reserves may be found in such tar sand formations.

In some instances these tar sand deposits are currently extracted via open-pit mining. Another approach for in situ extraction for deeper deposits is known as Steam-Assisted Gravity Drainage (SAGD). The heavy oil is immobile at reservoir temperatures and therefore the oil is typically heated to reduce its viscosity and mobilize the oil flow. In SAGD, pairs of injector and producer wells are formed to be laterally extending in the ground. Each pair of injector/producer wells includes a lower producer well and an upper injector well. The injector/production wells are typically located in the payzone of the subterranean formation between an underburden layer and an overburden layer.

The upper injector well is used to typically inject steam, and the lower producer well collects the heated crude oil or bitumen that flows out of the formation, along with any water from the condensation of injected steam. The injected steam forms a steam chamber that expands vertically and horizontally in the formation. The heat from the steam reduces the viscosity of the heavy crude oil or bitumen which allows it to flow down into the lower producer well where it is collected and recovered. The steam and gases rise due to their lower density so that steam is not produced at the lower producer well and steam trap control is used to the same affect. Gases, such as methane, carbon dioxide, and hydrogen sulfide, for example, may tend to rise in the steam chamber and fill the void space left by the oil defining an insulating layer above the steam. Oil and water flow is by gravity driven drainage, into the lower producer well.

Operating the injection and production wells at approximately reservoir pressure may address the instability problems that adversely affect high-pressure steam processes. SAGD may produce a smooth, even production that can be as high as 70% to 80% of the original oil in place (OOIP) in suitable reservoirs. The SAGD process may be relatively sensitive to shale streaks and other vertical barriers since, as the rock is heated, differential thermal expansion causes fractures in it, allowing steam and fluids to flow through. Moreover, hydrocarbon reservoirs may be inhomogeneous may include "thief zones" which may allow steam to escape in the SAGD wells. Local regions of relatively poor formation permeability may also be disadvantageous for hydrocarbon extraction. SAGD may be twice as efficient as the older cyclic steam stimulation (CSS) process.

Many countries in the world have large deposits of oil sands, including the United States, Russia, and various countries in the Middle East. Oil sands may represent as much as two-thirds of the world's total petroleum resource, with at least 1.7 trillion barrels in the Canadian Athabasca Oil Sands, for example. At the present time, only Canada has a large-scale commercial oil sands industry, though a small amount of oil from oil sands is also produced in Venezuela. Because of increasing oil sands production, Canada has become the largest single supplier of oil and products to the United States. Oil sands now are the source of almost half of Canada's oil production, although due to the 2008 economic downturn work on new projects has been deferred, while Venezuelan production has been declining in recent years. Oil is not yet produced from oil sands on a significant level in other countries.

U.S. Published Patent Application No. 2010/0078163 to Banerjee et al. discloses a hydrocarbon recovery process whereby three wells are provided: an uppermost well used to inject water, a middle well used to introduce microwaves into the reservoir, and a lowermost well for production. A microwave generator generates microwaves which are directed into a zone above the middle well through a series of waveguides. The frequency of the microwaves is at a frequency substantially equivalent to the resonant frequency of the water so that the water is heated.

Along these lines, U.S. Published Application No. 2010/0294489 to Dreher, Jr. et al. discloses using microwaves to provide heating. An activator is injected below the surface and is heated by the microwaves, and the activator then heats the heavy oil in the production well. U.S. Published Application No. 2010/0294488 to Wheeler et al. discloses a similar approach. The radial penetration depth of microwaves may be insufficient for timely and economic recovery of hydrocarbon resources. For example, oil sand strata may be 10 or more meters thick, yet the depth of a 2450 MHz microwave for heating may penetrate about 9 inches.

U.S. Pat. No. 7,441,597 to Kasevich discloses using a radio frequency generator to apply RF energy to a horizontal portion of an RF well positioned above a horizontal portion of a oil/gas producing well. The viscosity of the oil is reduced as a result of the RF energy, which causes the oil to drain due to gravity. The oil is recovered through the oil/gas producing well.

To improve the SAGD process, for example, SAGD wells may be monitored, and more particularly, an injection process may be monitored, as disclosed by U.S. Pat. No. 7,640,133 to Monmont et al. A tool that includes a temperature sensor, a pressure sensor, and a flow rate meter is used for measuring temperature, pressure, and velocity at various measurement locations along an injector portion of a wellbore. The tool is conveyed along the wellbore by coiled tubing which is capable of being repeatedly coiled and uncoiled from a truckable spool. Unfortunately, long production times, for example, due to a failed startup, to extract oil using SAGD may lead to significant heat loss to the adjacent soil, excessive consumption of steam, and a high cost for recovery. Over fifty percent of failed startups, for example, are typically abandoned. Significant water resources are also typically used to recover oil using SAGD which impacts the environment. Limited water resources may also limit oil recovery. SAGD is also not an available process in permafrost regions, for example.

SUMMARY OF THE INVENTION

In view of the foregoing background, it is therefore an object of the present invention to provide a method for more efficiently recovering hydrocarbon resources from a subterranean formation and while potentially using less energy and/or water resources and providing faster recovery of hydrocarbons.

This and other object, features, and advantages in accordance with the present invention are provided by a method of hydrocarbon resource recovery from a subterranean formation that includes forming a plurality of spaced apart injector/producer well pairs in the subterranean formation. Each injector/producer well pair includes a laterally extending producer well and a laterally extending injector well spaced thereabove, for example. The method includes forming an intermediate well adjacent a given injector/producer well pair, and operating a positioning actuator to position a radio frequency (RF) sensor coupled to the positioning actuator to a predetermined location within the intermediate well. The method also includes operating the RF sensor at the predetermined location within the intermediate well to selectively sense a corresponding portion of the subterranean formation adjacent the given injector/producer well pair, for example. The method further includes recovering hydrocarbon resources from the plurality of injector/producer well pairs including the given injector/producer well pair, for example. Accordingly, portions of the subterranean formation may be selectively sensed to more efficiently recover hydrocarbon resources, such as, for example, to identify a failed well at a failed location.

The RF sensor may include a transmission line having a proximal end coupled to the positioning actuator. The RF sensor may also include an antenna coupled to a distal end of the transmission line.

An apparatus aspect is directed to an apparatus for a subterranean formation that includes a plurality of spaced apart injector/producer well pairs in the subterranean formation, wherein each injector/producer well pair includes a laterally extending producer well and a laterally extending injector well spaced thereabove, and an intermediate well adjacent a given injector/producer well pair. The apparatus may include a radio frequency (RF) analyzer and an RF sensor coupled to the RF analyzer. The apparatus may also include a positioning actuator coupled to the RF sensor and configured to position the RF sensor to at least one predetermined location within the intermediate well so that the RF sensor is operable at the at least one predetermined location within the intermediate well to selectively sense at least one corresponding portion of the subterranean formation adjacent the given injector/producer well pair, for example.

BRIEF DESCRIPTION OF THE DRAWINGS

FIG. 6b is an enlarged cross-sectional view of a portion of the RF applicator in FIG. 6a.

FIG. 9b is a enlarged cross-sectional view of a portion of the RF sensor in FIG. 9a.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notation is used to indicate similar elements in alternative embodiments.

Figure 1:
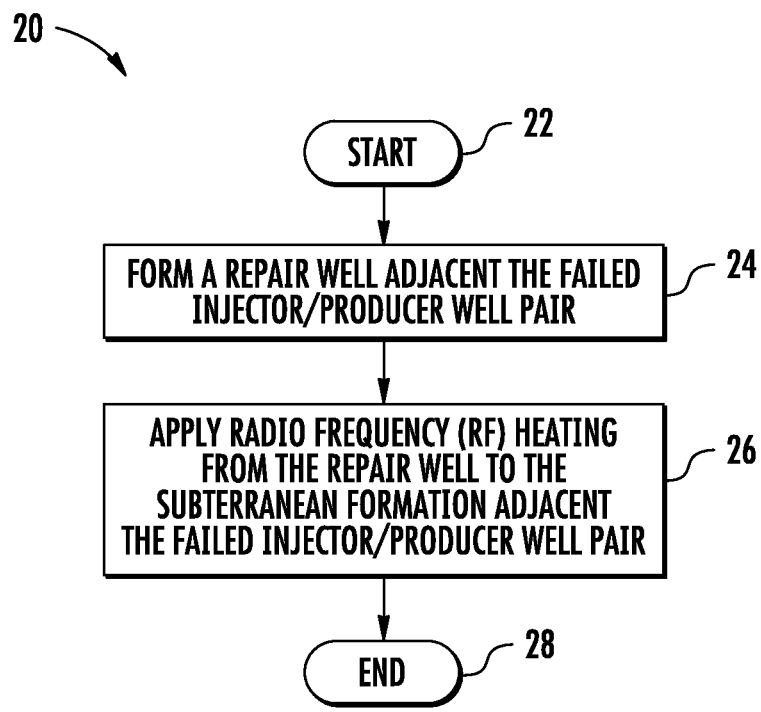
FIG. 1 is a flow chart of a method of repairing a failed injector/producer well pair in accordance with the present invention.
Figure 2:
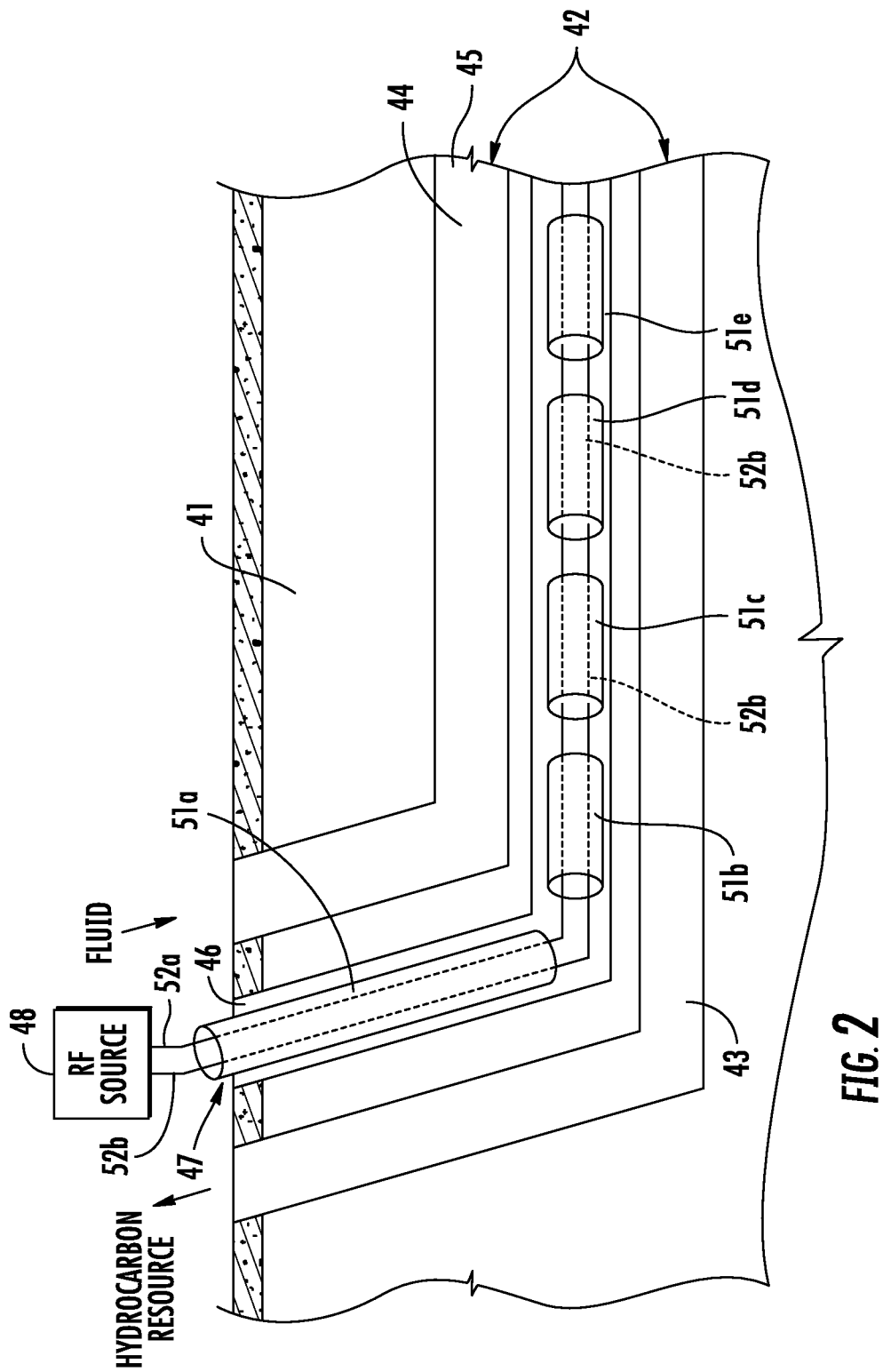
FIG. 2 is a schematic diagram of a hydrocarbon resource recovery arrangement for use with the method of FIG.

Referring initially to the flowchart 20 in FIG. 1, and FIG. 2, beginning at Block 22, a method of repairing a failed injector/producer well pair 42 from among a plurality of spaced apart injector/producer well pairs in a subterranean formation 41 is now described. Each injector/producer well pair includes a laterally extending producer well 43 and a laterally extending injector well 44 spaced thereabove as illustrated. The method includes, at Block 24, forming a repair well 46 adjacent the failed injector/producer well pair 42. More particularly, the repair well 46 may be formed between each well of the failed injector/producer well pair 42.

A well pair 42 may fail because of insufficient hydrocarbon resource, i.e. bitumen, mobility, for example. In particular, convective flow may convey steam heat, but it may be increasingly difficult to initiate this flow at the outset. RF heating may provide initial softening of the hydrocarbon resource to initiate convective flow. In particularly cold subterranean formations, when steam is used, the relatively high hydrocarbon resource viscosity may not allow any steam to penetrate the subterranean formation through the laterally extending injector well 44, or the steam may escape at an undesired location. Other reasons for an injector/producer well pair 42 to fail will be appreciated by those skilled in the art.

At Block 26, the method includes applying radio frequency (RF) heating from the repair well 46 to the subterranean formation 41 adjacent the failed injector/producer well pair 42. As will be appreciated by those skilled in the art, the RF heating may soften or improver permeability of the hydrocarbon resource to allow the desired operation of the failed injector/producer well pair 42 so that hydrocarbon resources may be recovered from the laterally extending producer well 43. In other words, the RF heating may be applied to increase, for example, improve or establish, hydraulic communication between the failed injector/producer well pair 42 along a length thereof to repair the failed injector/producer well pair. The method ends at Block 28.

Figure 3:
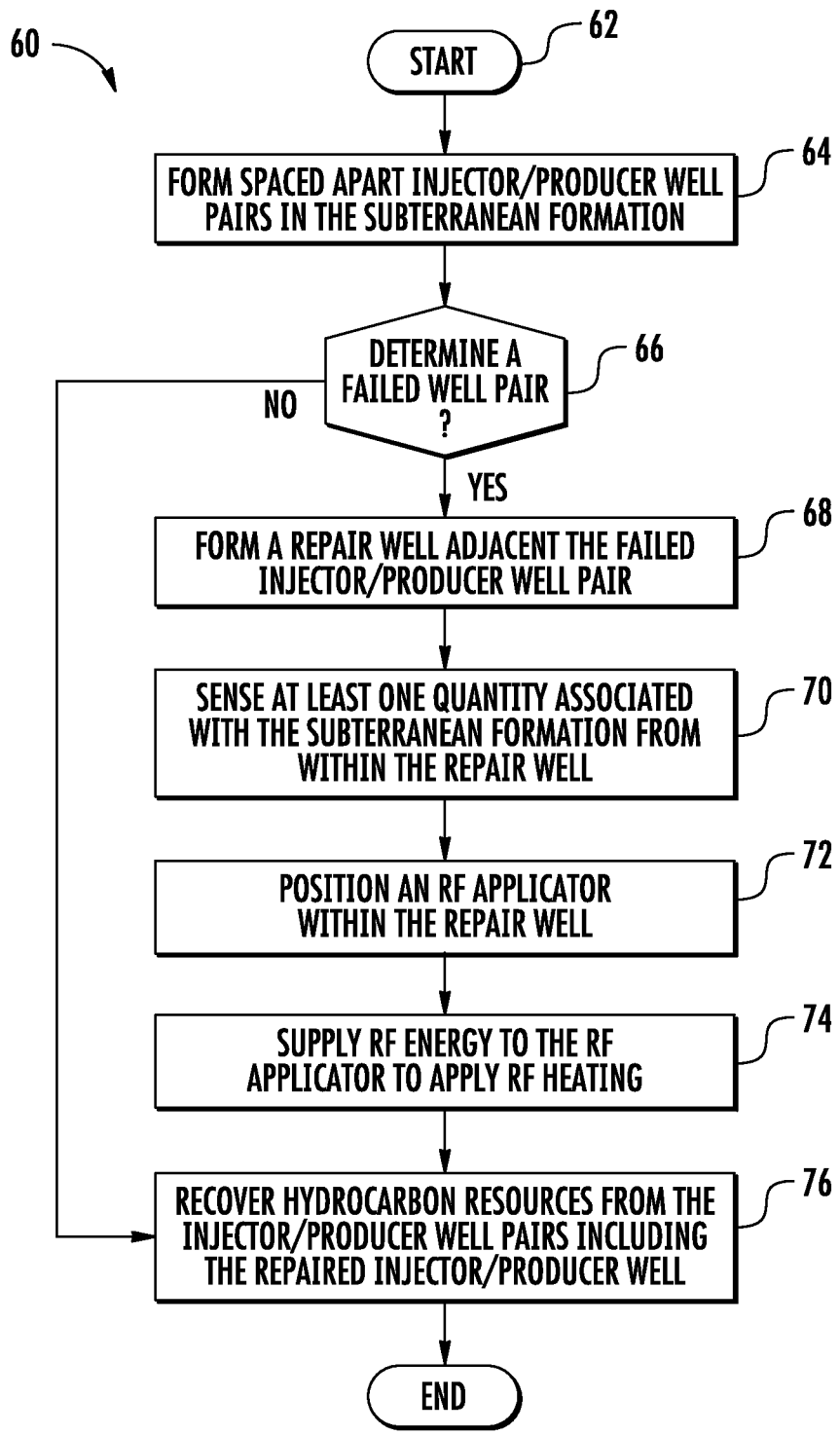
FIG. 3 is a flow chart of a method of hydrocarbon resource recovery in accordance with the present invention.

Referring now additionally to the flowchart 60 in FIG. 3, beginning at Block 62, the method of hydrocarbon resource recovery includes forming spaced apart injector/producer well pairs in a subterranean formation 41 (Block 64). The subterranean formation 41 may include an oil sand formation, for example. Each injector/producer well pair 42 includes a laterally extending producer well 43 and laterally extending injector well 44 spaced above the laterally extending injector well.

The method also includes, at Block 66, determining a failed well pair 42 from among the spaced apart injector/producer well pairs. The determination of whether a well pair has failed may be based upon one or more of a fluid flow and a temperature associated with the failed injector/producer well pair 42. For example, a fluid that may include a gas (e.g., steam), liquid, or combination of gas and liquid, that may be injected into the laterally extending injector well 44 may not flow properly into the subterranean formation 41 when steam, for example, escapes from a location other than a distal end 45 thereof. Additionally, for example, a temperature reading at the injector or producer wells 43, 44 may indicate that steam may not flow properly in the injector, producer, or into the subterranean formation 41.

Other indicia of a failure may include insufficient or no fluid flow, for example. One way, in particular, of determining whether the well pair 42 has failed is by measuring a back pressure of the injector well 44. A failed well pair 42 may be determined using other techniques, as will be appreciated by those skilled in the art.

As noted above, a well pair may fail because of insufficient hydrocarbon resource, i.e. oil, mobility, for example. In particularly cold subterranean formations, when steam is used, the relatively high hydrocarbon viscosity may not allow any steam to flow, or the steam may escape at an undesired location. Conduction, for starting convection, is often unreliable, as steam may escape to a "thief zone" or the surface, for example. Other reasons for an injector/producer well pair to fail will be appreciated by those skilled in the art.

Once a well pair has been determined as being failed, the method further includes repairing the failed injector/producer well pair 42. Repairing the failed injector/producer well pair 42 includes, at Block 68, forming a repair well 46 adjacent the failed injector/producer well. The repair well 46 is also laterally extending in the subterranean formation 41 and is positioned between the failed injector/producer well pair 42. Of course, as will be appreciated by those skilled in the art, the repair well 46 may be positioned in another configuration adjacent the failed injector/producer well pair 42.

In some embodiments, repairing the failed injector/producer well 42 may include optionally sensing a quantity associated with the subterranean formation 41 from within the repair well 46 (Block 70). The sensed quantity may be an impedance, for example. The sensed quantity may be particularly advantageous for determining a location of the failure, as will be appreciated by those skilled in the art. Further details of sensing will be explained below.

RF heating is applied from the repair well 46 to the subterranean formation 41 adjacent the failed injector/producer well pair 42. More particularly, an RF applicator 47 is positioned within the repair well 46 (Block 72).

Positioning of the RF applicator 47 may be based upon the sensing, for example. In some embodiments, the RF applicator 47 may be positioned to a predetermined location within the repair well to selectively apply RF heating to the corresponding portion of the subterranean formation. This may be particularly advantageous, for example, when the failure of the failed injector/producer well pair 42 has been isolated to the predetermined location, as will be appreciated by those skilled in the art.

RF energy is supplied from an RF source 48 above the subterranean formation 41 to the RF applicator 47 (Block 74) to apply the RF heating. RF heating may be applied to increase hydraulic communication between the failed injector/producer well pair 42 along an entire length thereof. More particularly, RF heating may be applied so that fluid that may be injected into the injector well 44 may result in hydrocarbon resources being collected at the producer well 43, for example, as in steam assisted gravity drainage (SAGD) recovery. As will be appreciated by those skilled in the art, the RF heating may soften or improve the permeability of the hydrocarbon resource to allow the desired fluid flow.

The RF applicator 47 illustratively includes tubular conductors 51*a*-51*e* arranged in end-to-end relation. The laterally extending tubular conductors 51*b*-51*e* may have a length sized to be at a natural resonance at a desired operating frequency of the RF source 48. The length corresponding to the natural resonance may be about a half-wavelength of a desired operating frequency of the RF source 48, and may be determined according to the equation $l=c/2f\sqrt{\in_r}$, where l is the length of each tubular conductor 51*a*, c is the speed of light, f is the frequency of the RF source, and $\in_r$ is the dielectric permittivity of the subterranean formation 41. A typical operating frequency range is about 3-30 MHz, for example. The tubular conductors 51*a*-51*e* may include a metallic material, for example.

The RF applicator 47 also includes a pair of spaced apart feed conductors 52*a*, 52*b* that extend the length of the repair well 46 and within the tubular conductors 51*a*-51*e*. The pair of spaced apart feed conductors 52*a*, 52*b* is coupled to the tubular conductors 51*a*-51*e* at each tubular conductor. More particularly, the first feed conductor 52*a* is coupled to a proximal end of each tubular conductors 51*a*-51*e*, and the second feed conductor 52*b* is coupled to the distal end of each tubular conductor 51*a*-51*e* (FIG. 2). The pair of spaced apart feed conductors 52*a*, 52*b* may be in the form of a twinaxial cable, for example.

Figure 4:
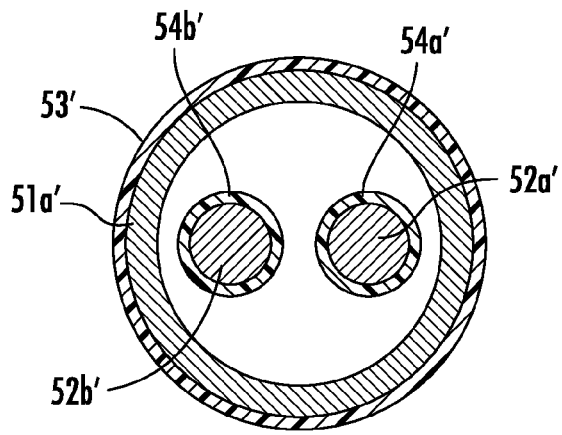
FIG. 4 is a cross-sectional view of a portion of an RF applicator of according to an embodiment of the present invention.

Referring now to FIG. 4, in another embodiment, a dielectric layer 53' may be on each tubular conductor 51*a'*. More particularly, the dielectric layer 53' may surround an outer portion of each tubular conductor 51*a'*. Insulating each tubular conductor 51*a'* from the adjacent subterranean formation 41' may advantageously result in increased electrical load resistance and a reduced size for the spaced apart feed conductors 52*a'*, 52*b'*. Alternatively, each tubular conductor 51*a'* may be configured without electrical insulation, and larger gauge spaced apart feed conductors 52*a'*, 52*b'* may be used. More or less tubular conductors 51*a'* may be used based upon the length of the repair well 46'. Additionally, each of the pair of spaced apart feed conductors 52*a'*, 52*b'* also includes a respective dielectric layers 54*a'*, 54*b'*. In other words, each of the pair of spaced apart feed conductors 52*a'*, 52*b'* is also electrically insulated.

Further details of the RF applicator may be found in application Ser. No. 12/950,339 filed Nov. 19, 2010, which is assigned to the assignee of the present application, and the entire contents of which are herein incorporated by reference. Of course, other types and configurations of RF applicators may be used.

After the well pair 42 has been repaired, or if was determined at Block 66 that the well pair has not failed, the hydrocarbon resource is recovered from the injector/producer well pairs including the repaired injector/producer well pair 42 (Block 76). As described above, the hydrocarbon resource may be recovered using SAGD, for example. Other techniques for hydrocarbon resource recovery may be used such as using hot water instead of steam may be used as will be appreciated by those skilled in the art. The method ends at Block 78.

Figure 5:
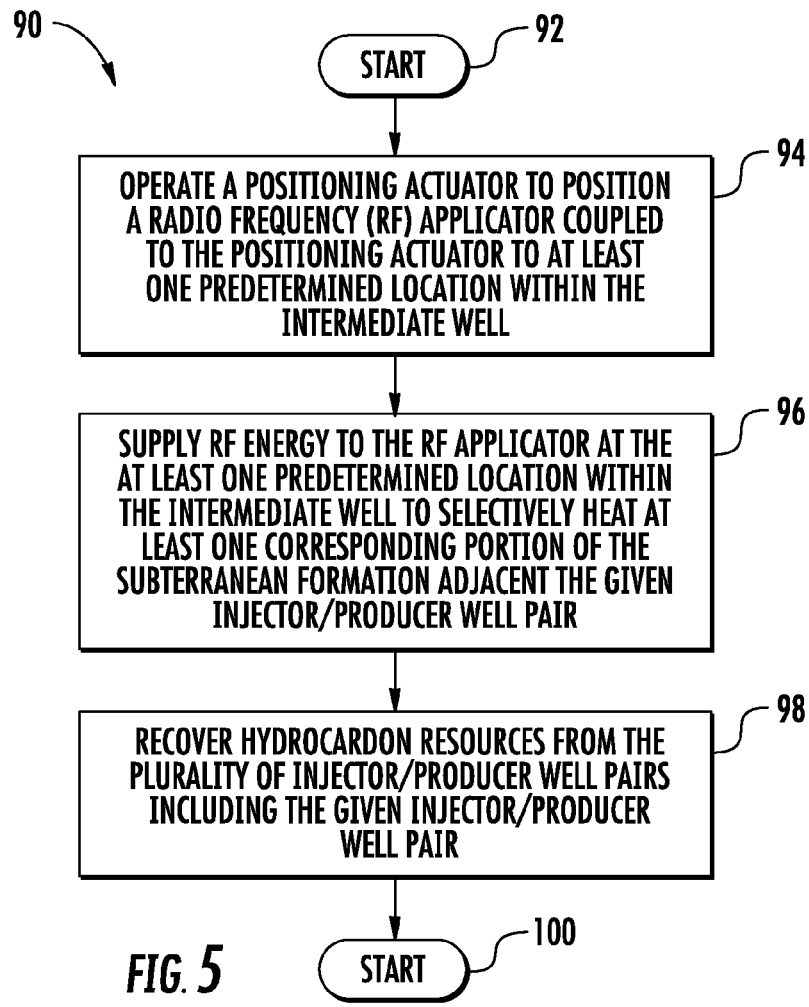
FIG. 5 is a flow chart of a method of hydrocarbon resource recovery according to another embodiment of the present invention.
Figure 6A:
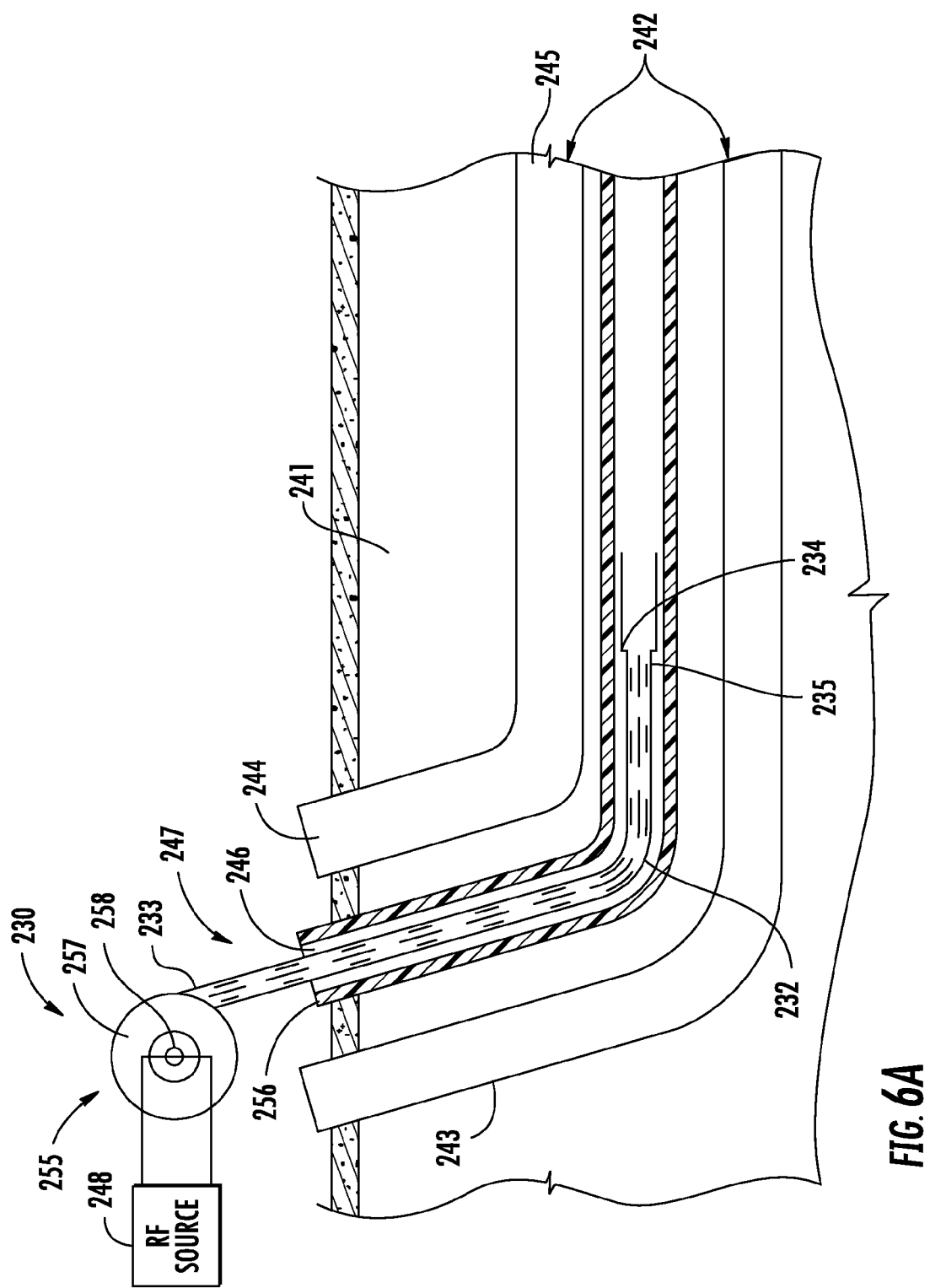
FIG. 6a is a schematic diagram of a hydrocarbon resource arrangement for use with the method of FIG. 5.

Referring now to the flowchart 90 in FIG. 5 and FIG. 6*a* another advantageous embodiment is now described. Beginning at Block 92, the method is for hydrocarbon resource recovery in a subterranean formation 241 including a plurality of spaced apart injector/producer well pairs in the subterranean formation, wherein each injector/producer well pair includes a laterally extending producer well 243 and a laterally extending injector well 244 spaced thereabove, and an intermediate well 246 is adjacent a given injector/producer well pair. The subterranean formation 241 may include an oil sand formation, for example.

The method includes operating a positioning actuator 255 to position a radio frequency (RF) applicator 247 coupled to the positioning actuator to a predetermined location within the intermediate well 246 (Block 94). The predetermined location may be failure location in a failed injector/producer well pair, for example. In other words, the given injector/producer well pair 242 may be a failed injector/producer well pair.

The method also includes, at Block 96, supplying RF energy from an RF source 248 to the RF applicator 247 at the predetermined location within the intermediate well 246 to selectively heat the corresponding portion of the subterranean formation 241 adjacent the given injector/producer well pair 242. The RF energy may be supplied to increase hydraulic communication between the given injector/producer well pair 242, for example. More particularly, RF energy may be applied so that fluid injected into the injector well 244 may result in hydrocarbon resources being collected at the producer well 243, for example, as in SAGD. As will be appreciated by those skilled in the art, the RF energy may soften or improve the permeability of the hydrocarbon resource to allow the desired hydrocarbon recovery and/or fluid flow.

The method also includes recovering hydrocarbon resources from the plurality of injector/producer well pairs including the given injector/producer well pair 242 (Block 98). As described above, the hydrocarbon resource may be recovered using SAGD, for example. Other techniques for hydrocarbon resource recover may be used, for example, solvent assisted techniques, miscible processes, gas drive techniques, and hot-water drive techniques, as will be appreciated by those skilled in the art. The method ends at Block 100.

Figure 6B:
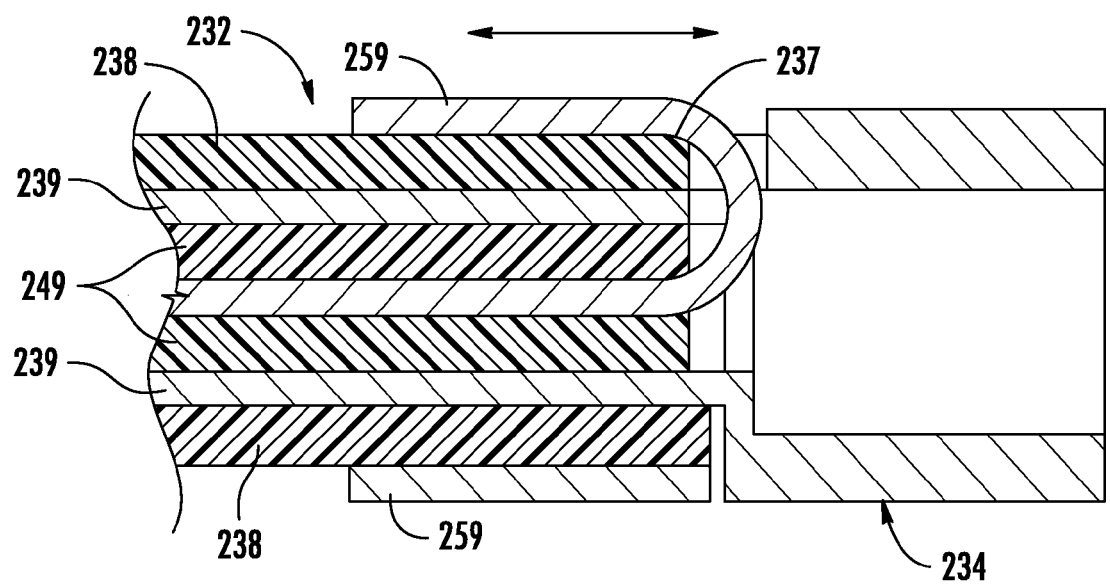
Figure 7:
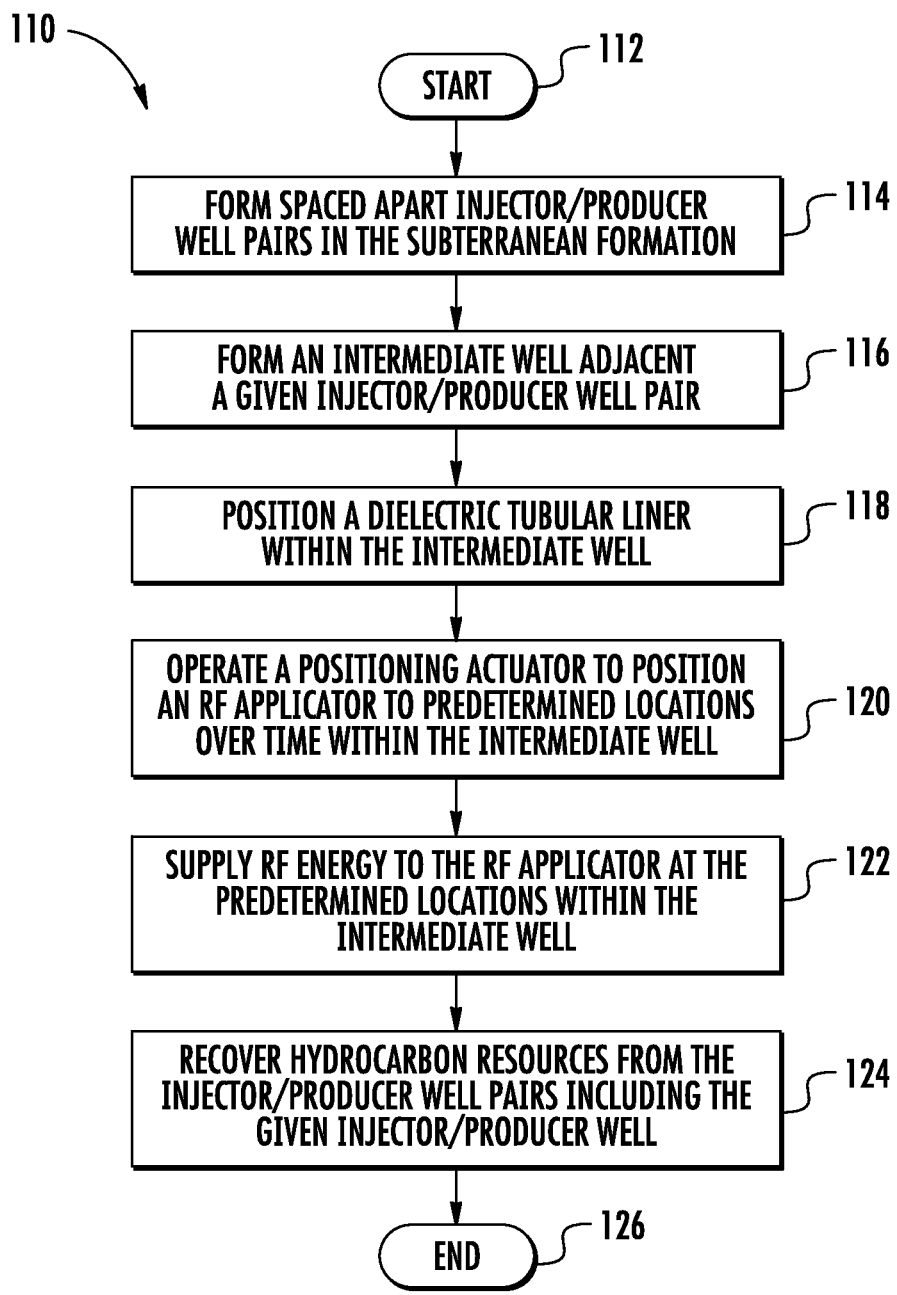
FIG. 7 is a more detailed flow chart of the method of hydrocarbon resource recovery of FIG. 5.

Referring now additionally to FIG. 6b, and the flowchart 110 in FIG. 7, beginning at Block 112, the method of hydrocarbon resource recovery from a subterranean formation 241 includes forming a plurality of spaced apart injector/producer well pairs in the subterranean formation (Block 114). The subterranean formation 241 may include an oil sand formation, for example. Each injector/producer well pair includes a laterally extending producer well 243 and a laterally extending injector well 244 spaced thereabove. The method also includes forming an intermediate well 246 adjacent, and more particularly, between, a given injector/producer well pair 242 (Block 116).

At Block 118, the method optionally includes positioning a dielectric tubular liner 256 within the intermediate well 246. The dielectric tubular liner 256 may advantageously improve RF heating uniformity, as will be appreciated by those skilled in the art.

The method also includes operating a positioning actuator 255 to position the radio frequency (RF) applicator 247 coupled to the positioning actuator 255 to at least one predetermined location within the intermediate well 246. In particular, the method includes, at Block 120, operating the positioning actuator 255 to position the RF applicator 247 to predetermined locations over time. In other words, the RF applicator 247 is moveable within the intermediate well 246 along a length thereof by way of the positioning actuator 255.

The positioning actuator 255 may include a rotatable reel 257 and an electrical coupling arrangement 258 carried by the rotatable reel that may be advantageously driven by an electrical motor as would be appreciated by those skilled in the art. The electrical coupling arrangement 258 is coupled to the RF source 248 and may be in the form of slip rings, for example. The positioning actuator 255 may include other arrangements configured to position the RF applicator 247 within the intermediate well 246.

The RF applicator 247 illustratively includes a coaxial transmission line 232 having a proximal end 233 coupled at the positioning actuator 255. The positioning actuator 255 may hold or store the coaxial transmission line 232, which may be flexible. The coaxial transmission line 232 may have an outer shield tube of soft corrugated copper. For example, the transmission line 232 may be Heliax® Cable, available from by Commscope, Inc., of Hickory, N.C. In some embodiments, other types of transmission lines may be used, for example, a shielded transmission line. The RF applicator 247 also includes a dipole antenna 234 coupled to a distal end 235 of the coaxial transmission line 232.

In some embodiments, an end, for example, the distal end 235 of the coaxial transmission line 232 may form the dipole antenna 234. More particularly, the inner conductor 237 of the coaxial transmission line 232 may be coupled to a conductive tube 259 carried by the outer jacket or insulation 238, while the outer conductor 239 may extend beyond the end of the inner conductor to define the dipole antenna 234, for example (FIG. 6b). A dielectric layer 249 is illustratively between the inner and outer conductors 237, 239. The RF applicator 247 may include other types of transmission lines, for example, a triaxial cable, and may also include other types of antennas and antenna coupling arrangements, as will be appreciated by those skilled in the art.

At Block 122, the method includes supplying RF energy from the RF source 248 to the RF applicator 247 at the predetermined locations within the intermediate well 246 to selectively heat the corresponding portion of the subterranean formation 241 adjacent the given injector/producer well pair 242. In other words, the method includes supplying RF energy from the RF source 248 to the RF applicator 247 when positioned at the predetermined locations over time. RF energy may be supplied to the RF applicator 247 to heat the subterranean formation 241 and increase hydraulic communication between the given injector/producer well pair, for example.

The RF source 248 may generate about 100 to 500 kilowatts of power for selective application as in this embodiment, instead of power in the range of several megawatts as in those embodiments providing RF heating along the entire length of the well 246. This is because the RF energy is localized at the dipole antenna 234.

As will be appreciated by those skilled in the art, the method steps may be particularly useful for repairing the given injector/producer well pair 242 when they have failed. Additionally, moving the RF applicator 247 to different positions along the intermediate well 246 may be particularly useful for jump-starting hydrocarbon resource recovery, and/or for increased localized RF heating.

The method further includes recovering hydrocarbon resources from the plurality of injector/producer well pairs including the given injector/producer well pair 242 (Block 124). As described above, the hydrocarbon resource may be recovered using SAGD, for example. Other techniques for hydrocarbon resource recovery may be used, for example, solvent assisted techniques, miscible processes, gas drive techniques, and hot-water drive techniques, as will be appreciated by those skilled in the art. The method ends at Block 126.

The related hydrocarbon resource recovery apparatus 230 is for a subterranean formation 241 that includes spaced apart injector/producer well pairs in the subterranean formation, wherein each injector/producer well pair including a laterally extending producer well 243 and a laterally extending injector well 244 spaced thereabove, and an intermediate well 246 adjacent a given injector/producer well pair. The hydrocarbon resource recovery apparatus 230 includes a radio frequency (RF) applicator 247 and a positioning actuator 255 coupled to the RF applicator and configured to position the RF applicator to at least one predetermined location within the intermediate well 246. The hydrocarbon resource apparatus 230 also includes an RF source 248 coupled to the positioning actuator 255 and configured to supply RF energy to the RF applicator 247. The RF applicator 247 is configured to supply the RF energy to at least one predetermined location within the intermediate well 246 to selectively heat at least one corresponding portion of the subterranean formation 241 adjacent the given injector/producer well pair 242.

Figure 8:
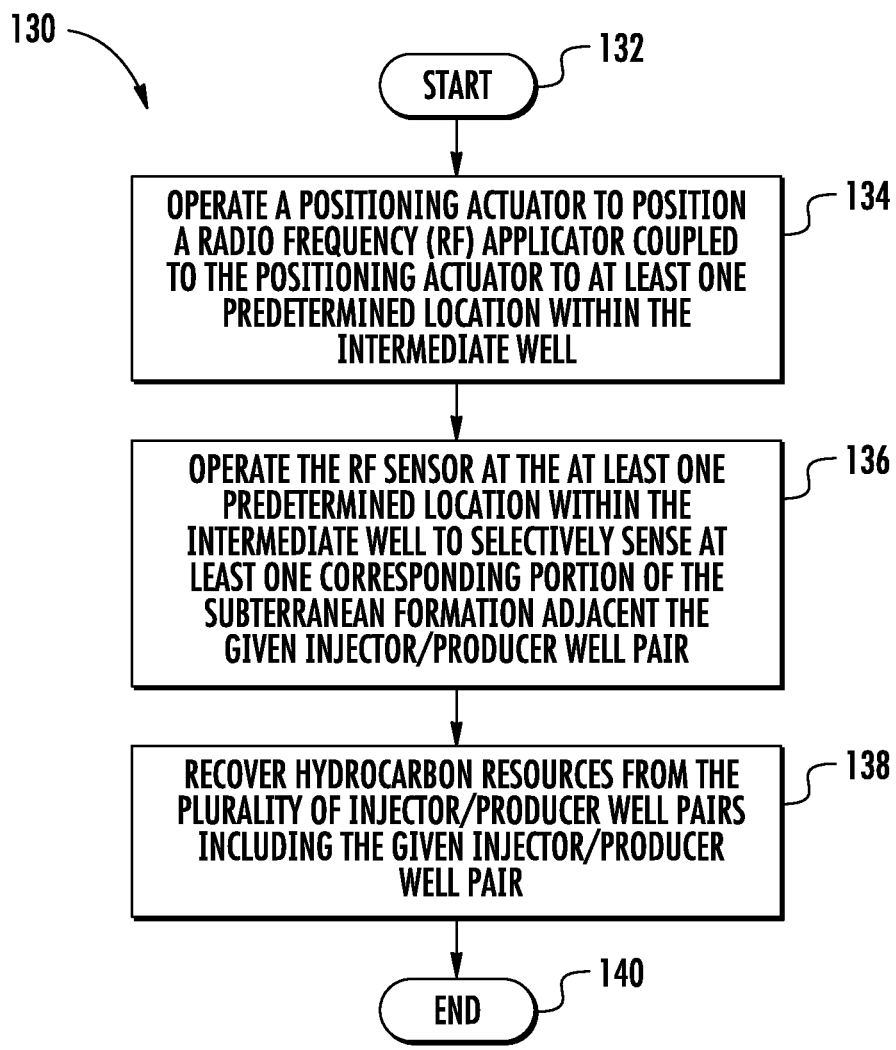
FIG. 8 is a flow chart of a method of hydrocarbon resource recovery according to another embodiment of the present invention.
Figure 9A:
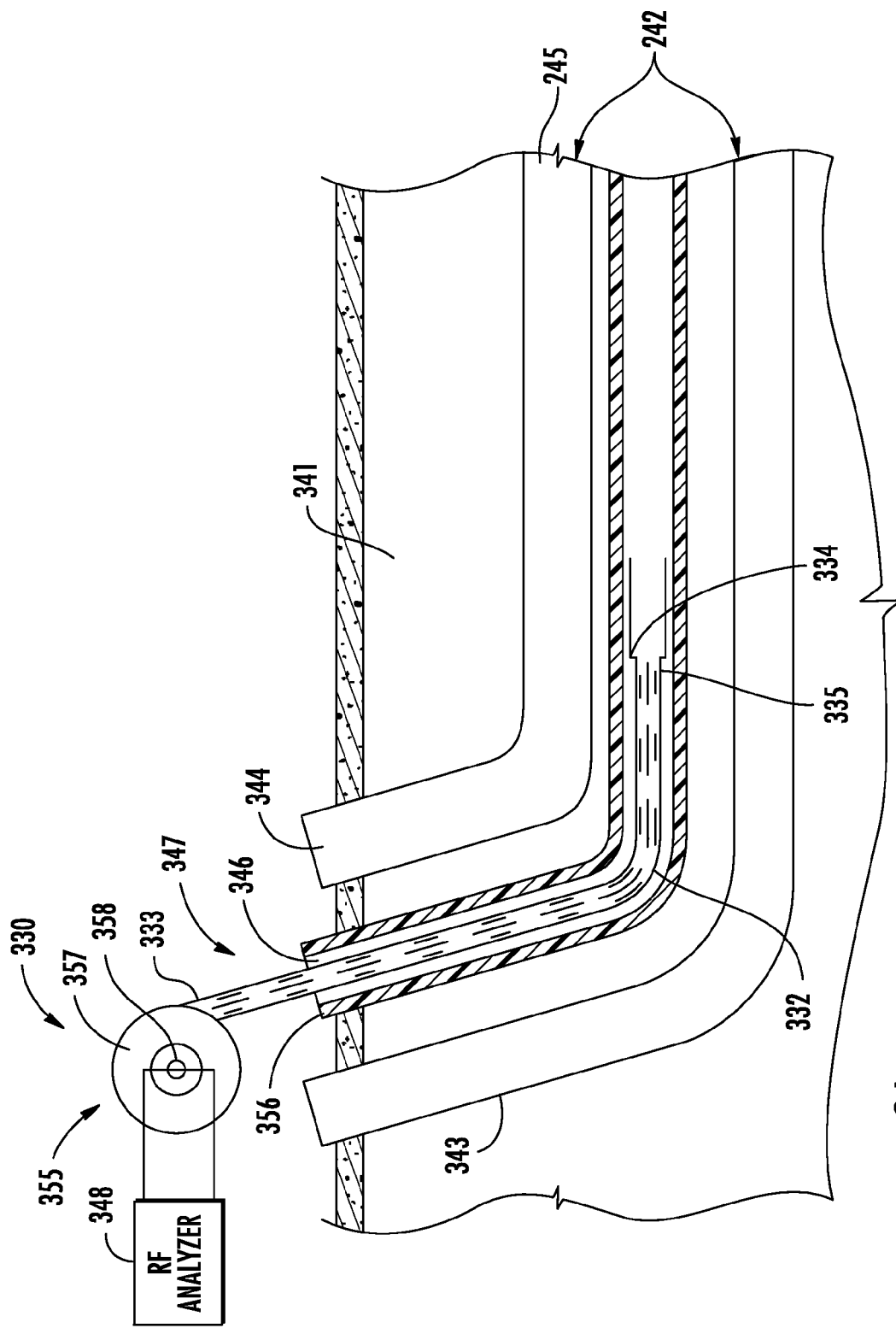
FIG. 9a is a schematic diagram of a hydrocarbon resource arrangement for use with the method of FIG. 8.

Referring now to the flowchart 130 in FIG. 8 and FIG. 9a another advantageous embodiment is now described. Beginning at Block 132, the method is for hydrocarbon resource recovery in a subterranean formation 341 including a plurality of spaced apart injector/producer well pairs in the subterranean formation, wherein each injector/producer well pair includes a laterally extending producer well 343 and a laterally extending injector well 344 spaced thereabove, and an intermediate well 346 adjacent a given injector/producer well pair. The subterranean formation 341 may include an oil sand formation, for example.

The method includes operating a positioning actuator 355 to position a radio frequency (RF) sensor 347 coupled to the positioning actuator to a predetermined location within the intermediate well 346 (Block 134). The predetermined location may be failure location in a failed injector/producer well pair, for example. In other words, the given injector/producer well pair 342 may be a failed injector/producer well pair.

The method also includes, at Block 136, operating the RF sensor 347 at the predetermined location within the intermediate well 346 to selectively sense the corresponding portion of the subterranean formation 341 adjacent the given injector/producer well pair 342. The sensed data is analyzed using an RF analyzer 348. The data from the RF sensor 347 may be analyzed to establish a profile of hydraulic communication between the given injector/producer well pair 342 along a length thereof, for example. More particularly, data from the RF sensor 347 may be analyzed prior to RF heating, for example, so that fluid injected into the injector well 344 may result in hydrocarbon resources being collected at the producer well 343, for example, as in SAGD. As will be appreciated by those skilled in the art, the sensed data may be used to build a profile to selectively heat the adjacent subterranean formation and thus soften the hydrocarbon resource to allow the desired hydrocarbon recovery and/or fluid flow.

The method also includes recovering hydrocarbon resources from the plurality of injector/producer well pairs including the given injector/producer well pair 342 (Block 138). As described above, the hydrocarbon resource may be recovered using SAGD, for example. Other techniques for hydrocarbon resource recovery may be used, as will be appreciated by those skilled in the art. The method ends at Block 140.

Figure 9B:
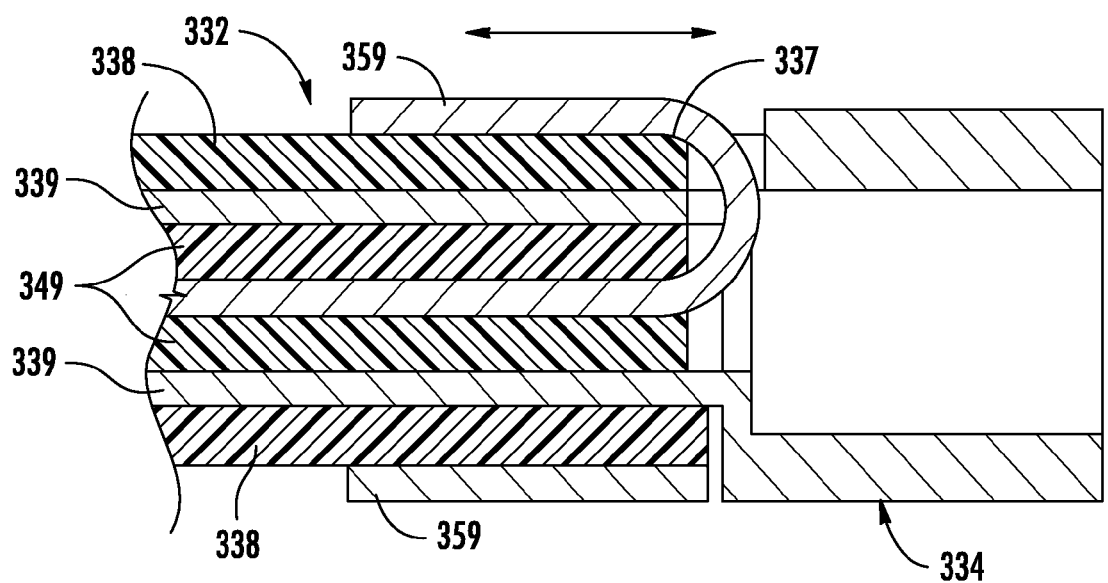
Figure 10:
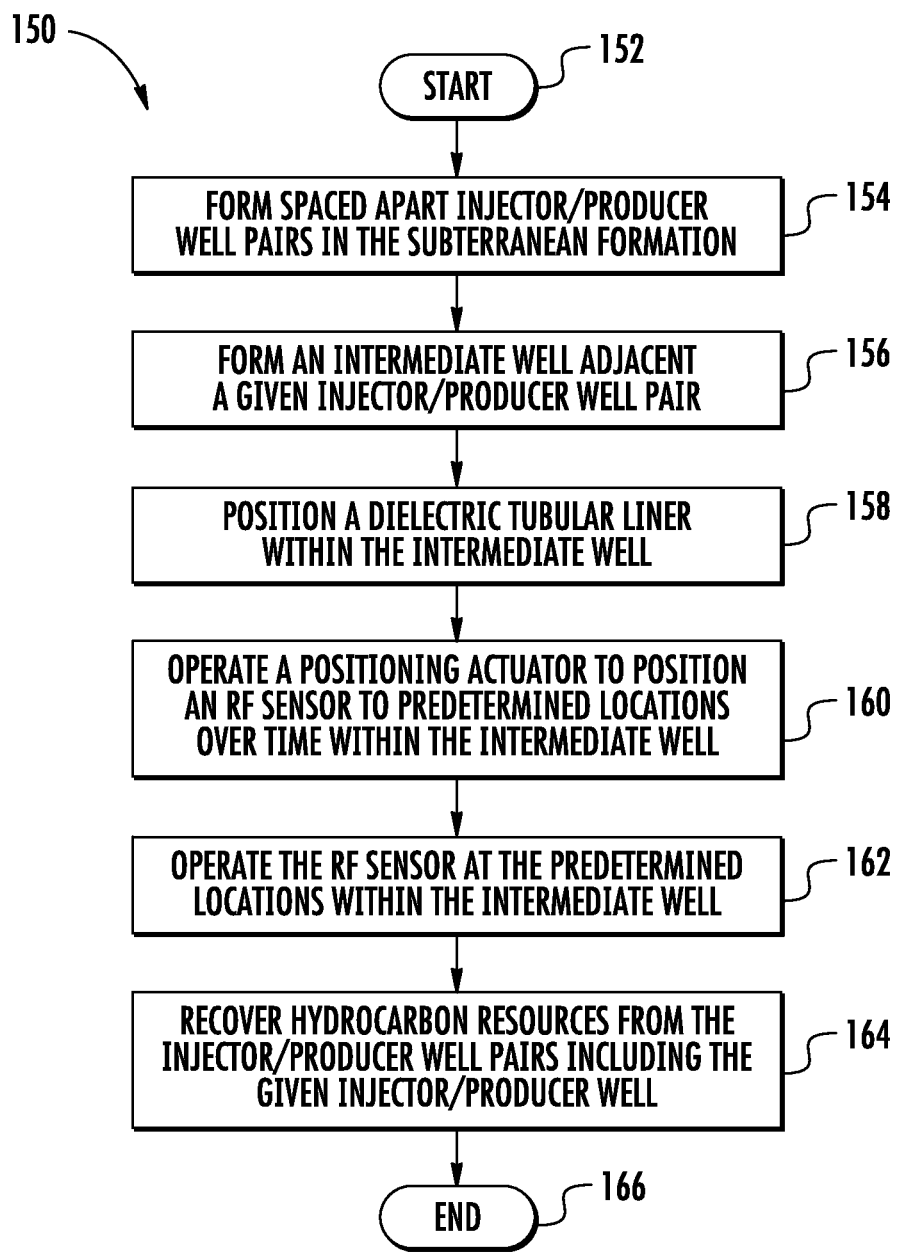
FIG. 10 is a more detailed flow chart of the method of hydrocarbon resource recovery of FIG. 8.

Referring now additionally to FIG. 9b, and the flowchart 150 in FIG. 10, beginning at Block 152, the method of hydrocarbon resource recovery from a subterranean formation 341 includes forming a plurality of spaced apart injector/producer well pairs in the subterranean formation (Block 154). The subterranean formation 341 may include an oil sand formation, for example. Each injector/producer well pair 342 includes a laterally extending producer well 343 and a laterally extending injector well 344 spaced thereabove. The method also includes forming an intermediate well 346 adjacent, and more particularly, between, a given injector/producer well pair 342 (Block 156).

At Block 158, the method optionally includes positioning a dielectric tubular liner 356 within the intermediate well 346. The dielectric tubular liner 356 may advantageously improve RF sensing uniformity, as will be appreciated by those skilled in the art.

The method also includes operating a positioning actuator 355 to position an RF sensor 347 coupled to the positioning actuator to predetermined locations within the intermediate well 346. In particular, the method includes, at Block 160, operating the positioning actuator 355 to position the RF sensor 347 to predetermined locations over time. In other words, the RF sensor 347 is moveable within the intermediate well 346 along a length thereof by way of the positioning actuator 355.

The positioning actuator 355 may include a rotatable reel 357 and an electrical coupling arrangement 358 carried by the rotatable reel. The electrical coupling arrangement 358 is coupled to the RF analyzer 348 and may be in the form of slip rings, for example. The positioning actuator 355 may include other arrangements configured to position the RF sensor 347 within the intermediate well 346.

The RE sensor 347 illustratively includes a coaxial transmission line 332 having a proximal end 333 coupled at the positioning actuator 355. The RF sensor 347 also includes a dipole antenna 334 coupled to a distal end 335 of the coaxial transmission line 332.

More particularly, the inner conductor 337 of the coaxial transmission line 332 may be coupled to a conductive tube 359 carried by the outer jacket or insulation 338, while the outer conductor 339 may extend beyond the end of the inner conductor to define the dipole antenna 334, for example (FIG. 9b). A dielectric layer 349 is illustratively between the inner and outer conductors 337, 339. The RF sensor 347 may include other types of transmission lines, for example, triaxial cable, and may also include other types of antennas and antenna coupling arrangements, as will be appreciated by those skilled in the art.

At Block 162, the method includes operating the RF sensor 347 at the predetermined locations within the intermediate well 346 to selectively sense the corresponding portion of the subterranean formation 341 adjacent the given injector/producer well pair 342. In other words, the method includes sensing data from the RF sensor 347 when positioned at the predetermined locations over time. Data associated with the subterranean formation 341 may be sensed by the RF sensor 347, for example, and using the RF analyzer 348 a profile of the adjacent subterranean formation may be determined. The profile of the sensed subterranean formation 341 may be used as a basis for selectively heating the subterranean formation at the predetermined locations within the intermediate well 346 to thus increase hydraulic communication between the given injector/producer well pair 342, for example.

The RF sensor 347 may cooperate with the RF analyzer 348 to measure and analyze an impedance, for example, of the adjacent subterranean formation. In some embodiments, time domain reflectometry may be used, for example, to sense and analyze an echo time of adjacent portions of the subterranean formation 341. Other types of sensors may be used in conjunction with or in addition to the RF sensor 347, such as, for example, an optical sensor, a temperature sensor, etc.

As will be appreciated by those skilled in the art, the method steps may be particularly useful for troubleshooting or repairing the given injector/producer well pair 342 when they have failed. Additionally, moving the RF sensor 347 to different positions along the intermediate well 346 may be particularly useful for localized sensing for use in jump-starting hydrocarbon resource recovery, and/or for increased localized RF heating.

The method further includes recovering hydrocarbon resources from the injector/producer well pairs including the given injector/producer well pair 342 (Block 164). As described above, the hydrocarbon resource may be recovered using SAGD, for example. Other techniques for hydrocarbon resource recover may be used, for example, solvent assisted techniques, miscible processes, gas drive techniques, and hot-water drive techniques, as will be appreciated by those skilled in the art. The method ends at Block 166.

The related hydrocarbon resource recovery apparatus 330 for a subterranean formation 341 that includes spaced apart injector/producer well pairs in the subterranean formation, wherein each injector/producer well pair comprising a laterally extending producer well 343 and a laterally extending injector well 344 spaced thereabove, and an intermediate well 346 adjacent a given injector/producer well pair. The hydrocarbon resource recovery apparatus 330 includes a radio frequency (RF) sensor 347 and a positioning actuator 355 coupled to the RF sensor and configured to position the RF sensor to at least one predetermined location within the intermediate well 346. The hydrocarbon resource apparatus 330 also includes an RF analyzer 348 coupled to the positioning actuator 355. The RF sensor 347 is configured to be operable to at the at least one predetermined location within the intermediate well 346 to selectively sense at least one corresponding portion of the subterranean formation 341 adjacent the given injector/producer well pair 342.

Further details and benefits of hydrocarbon resource recovery using RF heating are disclosed in U.S. Published Application No. 2013/0192825, assigned to the assignee of the present application, and the entire contents of which are herein incorporated by reference.

Features and components of the various embodiments disclosed herein may be exchanged and substituted for one another as will be appreciated by those skilled in the art. Many modifications and other embodiments of the invention will also come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An apparatus for a subterranean formation with a plurality of spaced apart injector/producer well pairs therein, each injector/producer well pair comprising a laterally extending producer well and a laterally extending injector well spaced thereabove, and an intermediate well adjacent a given injector/producer well pair, the apparatus comprising:
a radio frequency (RF) sensor;
a positioning actuator coupled to said RF sensor and configured to position said RF sensor within the intermediate well; and
an RF analyzer coupled to said RF sensor and configured to determine at least one failure location associated with the given injector/producer well pair by at least analyzing impedance data of the adjacent subterranean formation based upon diverging electric fields from said RF sensor to establish a resistivity based profile of hydraulic communication between the given injector/producer well pair along a length thereof, the diverging electric fields penetrating deeper within the subterranean formation than any magnetic fields associated with said RF sensor.

2. The apparatus according to claim 1, wherein said positioning actuator is configured to be positioned above the subterranean formation.

3. The apparatus according to claim 1, wherein said RF sensor comprises:
an RF transmission line having a proximal end coupled at said positioning actuator; and
an antenna coupled to a distal end of said RF transmission line.

4. The apparatus according to claim 3, wherein said positioning actuator comprises:
a rotatable reel configured to store and payout said RF transmission line; and
an electrical coupling arrangement carried by said rotatable reel and coupled between said RF analyzer and said RF transmission line.

5. The apparatus according to claim 1, further comprising a dielectric tubular liner to be positioned within the intermediate well and receive said RF sensor therein.

6. An apparatus for a subterranean formation with a plurality of spaced apart injector/producer well pairs therein, each injector/producer well pair comprising a laterally extending producer well and a laterally extending injector well spaced thereabove, and an intermediate well adjacent a given injector/producer well pair, the apparatus comprising:
a radio frequency (RF) impedance sensor;
a positioning actuator coupled to said RF impedance sensor and configured to position said RF impedance sensor within the intermediate well; and
an RF analyzer coupled to said impedance RF sensor and configured to determine at least one failure location associated with the given injector/producer well pair by at least analyzing impedance data based upon diverging electric fields, from said RF impedance sensor to establish a resistivity based profile of hydraulic communication between the given injector/producer well pair along a length thereof, the diverging electric fields penetrating deeper within the subterranean formation than any magnetic fields associated with said RF impedance sensor.

7. The apparatus according to claim 6, wherein said positioning actuator is configured to be positioned above the subterranean formation.

8. The apparatus according to claim 6, wherein said RF impedance sensor comprises:
an RF transmission line having a proximal end coupled at said positioning actuator; and
an antenna coupled to a distal end of said RF transmission line.

9. The apparatus according to claim 8, wherein said positioning actuator comprises:
a rotatable reel configured to store and payout said RF transmission line; and
an electrical coupling arrangement carried by said rotatable reel and coupled between said RF analyzer and said RF transmission line.

10. The apparatus according to claim 6, further comprising a dielectric tubular liner to be positioned within the intermediate well and receive said RF impedance sensor therein.

11. An apparatus for a subterranean formation with a plurality of spaced apart injector/producer well pairs therein, each injector/producer well pair comprising a laterally extending producer well and a laterally extending injector well spaced thereabove, and an intermediate well adjacent a given injector/producer well pair, the apparatus comprising:
a radio frequency (RF) sensor comprising an RF transmission line and an antenna coupled to a distal end thereof;
a positioning actuator coupled to a proximal end of said RF transmission line and configured to position said antenna within the intermediate well; and
an RF analyzer coupled to the distal end of said RF transmission line and configured to determine at least one failure location associated with the given injector/producer well pair by at least analyzing impedance data based upon diverging electric fields from said antenna to establish a resistivity based profile of hydraulic communication between the given injector/producer well pair along a length thereof, the diverging electric fields penetrating deeper within the subterranean formation than any magnetic fields associated with said RF sensor.

12. The apparatus according to claim 11, wherein said positioning actuator is configured to be positioned above the subterranean formation.

13. The apparatus according to claim 11, wherein said positioning actuator comprises:
a rotatable reel configured to store and payout said RF transmission line; and
an electrical coupling arrangement carried by said rotatable reel and coupled between said RF analyzer and said RF transmission line.

14. The apparatus according to claim 11, further comprising a dielectric tubular liner to be positioned within the intermediate well and receive said RF sensor therein.

* * * * *